(12) United States Patent
Shah

(10) Patent No.: US 12,633,399 B2
(45) Date of Patent: May 19, 2026

(54) METHOD FOR DELIVERING SUSTAINABLE HEALTHCARE TO A PATIENT-POPULATION

(71) Applicant: Vayu Health, Portola Valley, CA (US)

(72) Inventor: Avni Shah, Portola Valley, CA (US)

(73) Assignee: Vayu Health

( * ) Notice: Subject to any disclaimer, the term of this patent is extended or adjusted under 35 U.S.C. 154(b) by 396 days.

(21) Appl. No.: 17/807,592

(22) Filed: Jun. 17, 2022

(65) Prior Publication Data

US 2022/0406445 A1     Dec. 22, 2022

Related U.S. Application Data

(60) Provisional application No. 63/212,051, filed on Jun. 17, 2021.

(51) Int. Cl.
| | |
|---|---|
| *G16H 40/20* | (2018.01) |
| *G06Q 40/08* | (2012.01) |
| *G16H 50/70* | (2018.01) |

(52) U.S. Cl.
CPC ............. *G16H 40/20* (2018.01); *G06Q 40/08* (2013.01); *G16H 50/70* (2018.01)

(58) Field of Classification Search
CPC ............................... G16H 40/20; G06Q 40/08
See application file for complete search history.

(56) References Cited

U.S. PATENT DOCUMENTS

| | | | |
|---|---|---|---|
| 2012/0310661 A1* | 12/2012 | Greene | ............... G06Q 10/087 |
| | | | 705/2 |
| 2019/0307405 A1* | 10/2019 | Terry | ..................... G16H 10/60 |
| 2021/0007645 A1* | 1/2021 | Nakatsugawa | ........ A61B 5/486 |
| 2023/0120861 A1* | 4/2023 | Choudhuri | .............. G06F 40/40 |
| | | | 705/2 |

* cited by examiner

*Primary Examiner* — Reginald R Reyes
(74) *Attorney, Agent, or Firm* — UltimatEdge IP Law Group, P.C.; Dean G. Stathakis

(57) ABSTRACT

The present specification discloses methods for delivering sustainable healthcare to a patient-population suffering from a chronic condition to improved healthcare outcomes. The disclosed methods comprises aligning stakeholders involved in delivering care to the patient-population based on common metrics of success; establishing an advance primary care team to liaison with the patient-population and a community where patient-population resides to facilitate a delivery of care program; identifying the patient-population by assessing one or more individuals suffering from the chronic condition by risk stratification parameters; and implementing a sustainable value-based payment scheme. The disclosed methods may further comprise a data management step that provides a data infrastructure that facilitates analysis and reporting to enable transparent data sharing of each patient-population member linked to outcomes and cost and/or a technology platform step that implements an interoperable and flexible healthcare framework that monitors delivery of care and healthcare outcome of each patient-population member.

21 Claims, 3 Drawing Sheets

METHOD FOR DELIVERING SUSTAINABLE HEALTHCARE TO A PATIENT-POPULATION

INTRODUCTION

This application is a 35 U.S.C. § 111 patent application that claims the benefit of priority and is entitled to the filing date pursuant to 35 U.S.C. § 119(e) of U.S. Provisional Patent Application 63/212,051, filed Jun. 17, 2021, the content of which is hereby incorporated by reference in its entirety.

The continued disparities, gaps in care, and lack of improvement in population health outcomes in those living with chronic conditions(s) over the last 20 years, despite new drugs, new technologies, and rising costs, are proof that our health ecosystem has to change fundamentally. More recent proof has manifested due to COVID, which has disproportionately impacted chronically ill people who have been poorly served by our healthcare ecosystem failures.

The United States has one of the highest costs of health-care in the world, spending significantly more on healthcare relative to other industrialized nations. In addition, the share of the economy spent on healthcare has been steadily increasing since the 1980s, and the U.S. now spends nearly twice as much on health care as a share of the economy compared to the average level spent by other developed countries. In 2018, U.S. healthcare costs were $3.6 trillion, an amount representing 17.7% of gross domestic product, and translating to an annual health care cost of $11,172 per person per year. That makes healthcare one of the country's largest industries and such spending is expected to continue growing. Health care costs have risen faster than the median annual income because health spending growth has outpaced economic growth, in part because of the greater use of medical technologies, significant increases in prices in the healthcare sector, and increased demand for services.

Despite spending more on healthcare than any other country, the U.S. population experiences worse chronic condition health outcomes than their international peers primarily because people are not receiving timely, high-quality team-based care, especially the poor. Despite rising costs, poor health outcomes and gaps in care for the U.S. population living with chronic conditions has had very little change over the last 20 years. For example, individuals with chronic conditions still do not receive 50% of what medical expert guidelines recommend, there is greater than 17-year delay in establishing best practices, and there is a high amount of clinical inertia despite clear protocols all which delay meeting treatment goals. For example, the U.S. has fewer physician visits, lower life expectancy, higher suicide rates, higher chronic disease burden, highest number of hospitalizations from preventable causes, and the highest rate of avoidable deaths relative to their peers in most other industrialized countries. It is estimated that 90% of the nation's $3.8 trillion in annual healthcare expenditures are for people with at least one chronic and mental health conditions with more than half of all American adults having at least one chronic condition. The sickest 5% of the U.S. population consumes 50% of total healthcare costs while the healthiest 50% only consume 3% of the nation's healthcare costs. Again, despite expensive care, there are unchanged health outcomes and gaps which illustrates that the U.S. healthcare ecosystem has to change fundamentally.

Our healthcare ecosystem failures have created barriers to implement, scale, and spread best practice chronic care programs known to improve outcomes and costs for U.S. chronic condition population. The U.S. healthcare ecosys-tem needs to change how it delivers chronic condition care by aligning and integrating key ecosystem pieces to accelerate the value-based care movement: financially incentivizing and aligning stakeholders, selecting patients for the right care based on continuous learning principles, paying for team based social and behavioral care, measuring, and linking care processes and health outcomes with cost data for better data driven decisions.

SUMMARY

The present specification discloses methods for delivering sustainable healthcare to a patient-population suffering from a chronic condition in order to improve healthcare outcomes. In aspects, the disclosed methods comprises aligning stakeholders involved in delivering care to the patient-population based on common metrics of success; identifying the patient-population by assessing one or more individuals suffering from the chronic condition by risk stratification parameters; establishing a primary care team to liaison with the patient-population and a community where patient-population resides to facilitate a delivery of care program; and implementing a value-based payment scheme. The disclosed methods may further comprise a data management step that provides a data infrastructure that facilitates analysis and reporting to enable transparent data sharing of each member of the patient-population linked to outcomes and cost and/or a technology platform step that implements an interoperable and flexible healthcare framework that enables and monitors delivery of care and healthcare outcome of each member of the patient-population.

BRIEF DESCRIPTION OF THE DRAWINGS

The accompanying drawings, which are incorporated in and constitute a part of this specification, illustrate aspects of the disclosed subject matter in at least one of its exemplary embodiments, which are further defined in detail in the following description. Features, elements, and aspects of the disclosure are referenced by numerals with like numerals in different drawings representing the same, equivalent, or similar features, elements, or aspects, in accordance with one or more embodiments. The drawings are not necessarily to scale, emphasis instead being placed upon illustrating the principles herein described and provided by exemplary embodiments of the invention. In such drawings.

DETAILED DESCRIPTION

Figure 1:
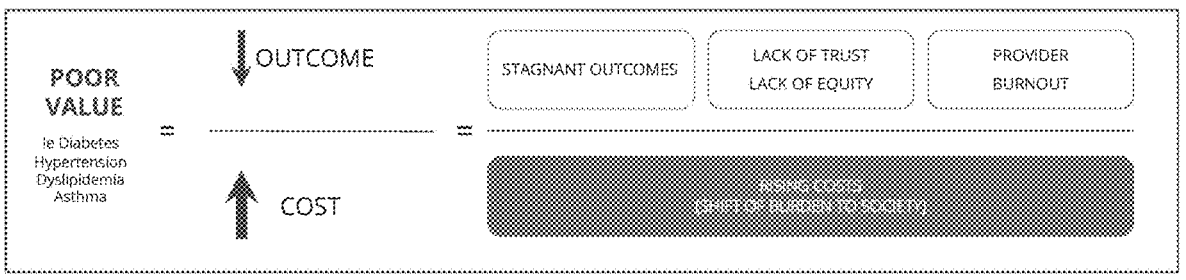
FIG. 1 shows a schematic of poor value as a function of poor healthcare outcomes and increasing cost.

Over the last 20 years, population health outcomes have not improved for individuals living with a chronic condition(s), especially for those with low incomes. This is despite new drugs, new technologies, and increased spending. The end result is poor value (poor outcomes with rising costs) for chronic conditions such as diabetes, hypertension, dyslipidemia, and asthma shown by stagnant population health outcomes, increasing lack of trust of the healthcare system, increasing disparities, and increasing provider burn-out, despite the continuously rising costs which shifts the burden to society (FIG. 1).

Figure 2:
FIG. 2 shows a schematic of current chronic condition care ecosystem.

Chronic care programs should include multiple elements, self-management, behavioral support, social support, deci-sion support, delivery system design, clinical information systems, healthcare organization, and community resources, which are known to improve health and disparities. Our healthcare ecosystem failures have created barriers to imple-ment, scale, and spread of chronic care programs to improve outcomes and costs for U.S. chronic condition population. As shown in FIG. 2, the six key steps that are not working together to create an innovative healthcare ecosystem for the patients most in need are: stakeholder alignment, sustainable best practice chronic care program, a value-based payment (VBP) scheme, target population, data management, and technology platform. As these steps have not been fully developed or designed to fit together, it has created a poorly functioning health ecosystem which is a reason of why it has been difficult to implement, sustain, maintain fidelity, scale, and spread best practice chronic care programs. This has contributed to the lack of chronic condition population health improvement in health, equity, experience, and cost.

Fundamental change is required to design and develop solutions to address these underlying systemic failures to sustain, scale, and spread a best practice chronic care pro-gram. The key ecosystem pieces are not fully developed and not designed to work together in a coordinated and sustain-able fashion due to a lack of alignment of incentives and accountability.

Figure 3:
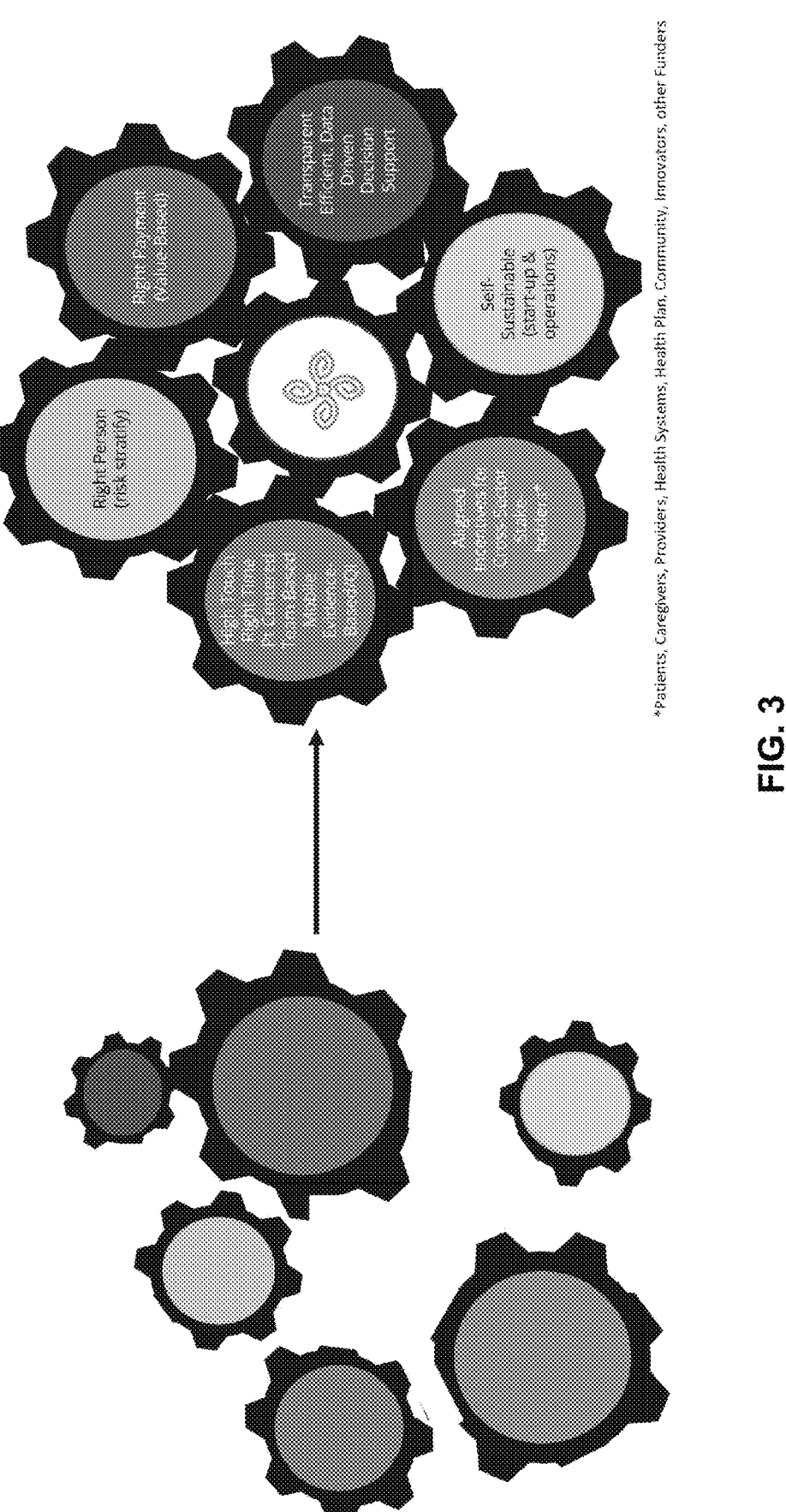
FIG. 3 shows a schematic of a chronic condition care ecosystem disclosed herein.

The disclosed method for delivering sustainable health-care to a patient-population suffering from a chronic condi-tion has aligned incentives with unique stakeholders, e.g., health plan providers (e.g., Medicaid managed care health plan providers), healthcare delivery organizations (e.g., executives, healthcare providers, and administrators of hos-pitals and community health clinics), state healthcare policy makers, and non-profit healthcare funders, to build a func-tional and integrated healthcare ecosystem that improves healthcare value, including, without limitation, improved health outcomes, improved access to healthcare, improved trust, decreased emergency room visits, and decreased hos-pitalizations) (FIG. 3). It is a best practice chronic care program (with a unique combination of a community clinic primary care physician with the program's behavioral thera-pist, educator, and local coach for in-person and virtual care) which is to be sustained with a newly developed VBP, which will allow development of a new sustainable business model that will "plug and play" to accelerate scale and spread to improve health, equity, experience, and cost within different community clinics. As shown in FIG. 3, the six key steps to create an innovative healthcare ecosystem for the patients most in need are: stakeholder alignment, sustainable best practice chronic care program, value-based payment scheme, target population, data management, and technol-ogy platform.

A disclosed method for delivering sustainable healthcare to a patient-population suffering from a chronic condition comprises aligning all stakeholders involved in delivering care to a patient. Such stakeholders include, without limi-tation, health plan providers (e.g., Medicaid managed care health plan providers), healthcare delivery organizations (e.g., executives, healthcare providers, and administrators of hospitals and community health clinics), state healthcare policy makers, and non-profit healthcare funders. Currently, there is systemic misalignment on what constitutes success-ful delivery of healthcare, e.g., in terms of the metrics used to assess quality, costs, and savings of healthcare provided, acceptable levels of costs associated with services provided, acceptable levels of payment received for services rendered, and acceptable mechanisms of cost savings. For example, healthcare plan providers and healthcare delivery organiza-tions are inherently antagonistic as the latter focuses on payment for the care delivered while the former continually stresses policies that reduce payments for the delivered care. In addition, healthcare plans typically decline to cover novel programs and the infrastructure/start-up costs associated with such programs, forcing healthcare delivery organiza-tions and vested healthcare providers to champion and implement programs based on individual healthcare delivery organization's incentives and ability to absorb start-up costs, unless the organization is fortunate enough to receive a government grant. Such tension can lead to 1) de-escalation of the program if the vested healthcare provider leaves or changes; 2) limited implementation of only a few chronic care program elements which aligned to specific strategic and often competitive needs 3) competitive needs limit the ability for sharing to scale to other healthcare delivery organizations. These consequences ultimately create distinc-tive programs that are unique and difficult to scale and spread outside of the healthcare delivery organization that created it. Furthermore, only large healthcare delivery orga-nizations can typically implement a novel program as it can commonly absorb start-up costs (in the midst of many other competing priorities) which do not need to be tracked so others could learn. In contrast, smaller healthcare delivery organizations often do not have finances for start-up costs to implement a novel program even if the desire and key healthcare providers are there.

A stakeholder alignment step disclosed herein establishes a collaboration of stakeholders from the start of the chronic care program to align on metrics of success including, without limitation, quality of healthcare delivered, schedule of costs and payments, schedule of savings, and distribution of funds. Such stakeholders include, without limitation, health plan providers (e.g., Medicaid managed care health plan providers), healthcare delivery organizations (e.g., executives, healthcare providers, and administrators of hos-pitals and community health clinics), state healthcare policy makers, and non-profit healthcare funders. Non-limiting examples of a healthcare provider include a doctor, a nurse, a behavioral therapist, an educator, or a coach. The stake-holder alignment step provides 1) the ability to all align on goals, measures, and payment to allow scaling and spread-ing; 2) the identification of short term outcome trends in disease specific health outcomes, engagement, reduced emergency room services and hospitalizations; 3) the assess-ment of the acceptability of all stakeholders; 4) the assess-ment of potential implementation risks and uncertainties which will help plan for mitigations; 5) the assessment of readiness and ability of stakeholders to change with different processes and systems; and 6) the assessment of community priorities to better integrate sustainable healthcare programs.

A disclosed method for delivering sustainable healthcare to a patient-population suffering from a chronic condition comprises establishing an advanced primary care team to liaison with the patient-population and a community where patient-population resides to facilitate a delivery of care program. Presently there is no effort to integrate all com-ponents tasked with delivering care to a patient requiring chronic care. Current programs of care delivery are health-care provider centric and not patient centric. For example, key chronic care components such as a team-based staff that facilitates effective integrated self-management, behavioral support, and social support are often not reimbursable and therefore, never implemented. In addition, many FFS care delivery systems are not paid to deploy many important services outside of the clinic (such as, e.g., home visits, virtual visits, behavioral care, population health best practices) or on the same day, especially Medicaid community clinics, unless under emergency situations (e.g., COVID). The lack of payment for outcomes discourages implementation of sustainable healthcare (e.g., through relationship building, healthcare teams, coaches, in-person and virtual services) to execute delivery of key chronic care components leads to inordinately prolonged and untimely treatment to chronic condition goals, high levels of missed appointments, and reduced access to care which enables poor outcomes.

A best practice chronic care program step disclosed herein is integrated in a community clinic which is unique as it utilizes known local community resources (e.g., food banks and volunteer-based community centers providing educational programs on health and well-being) and team based care which includes at a minimum a behavioral therapist, educator, primary care provider, and local coach to provide a human centered flexible advanced primary care team based chronic condition care refined on continuous learning principles. The team functions to delivers high-touch interactions (as much as every day) and proactive care that is trauma-informed, culturally sensitive, and whole-person. The advanced primary care team is charged with building a trusted relationship with the patient by focusing on and prioritizing patient's self-identified goals and establishing patient-led action plans, coordinating and delivering targeted risk reduction (e.g., optimize therapy) and cost-effective care. It also creates convenience and increased access for the patient by providing in-person and/or virtual care (e.g., home, church, community centers). The care program step includes 1) establishes composition and responsibilities for each member of the advanced primary care team; 2) assesses ideal scope of care to design a best practice care program (which includes) prioritizing self-identified goals of each member of the patient-population, ii) establishing patient-led action plans, iii) coordinating and delivering targeted risk reduction and cost-effective care, and iv) creating convenient and improved access for each member of the patient-population by providing in-person and/or virtual care); 3) develops methods to adapt the best practice care program to the community; 4) continuously monitors delivery of care to patient-population to identify barriers and best methods to improve delivery of care to each member of the patient-population; 5) continuously monitors delivery of care to patient-population to identify barriers and best methods to improve synchronous and asynchronous communication and collaboration between the advanced primary care team, the patient-population, and the community; and 6) assesses program training, workflow integration, protocols, and processes with the community clinic.

A disclosed method for delivering sustainable healthcare to a patient-population suffering from a chronic condition comprises identifying an appropriate target risk population for delivery of care. Since FFS payment schemes are volume based, there is no reason to account for health severity, health risks, social/behavioral risk, improvement in healthcare outcomes or costs, or access to healthcare. As such, patients are not stratified by total risk in outcomes and costs in order to determine the appropriate delivery of care for any particular patient. For example, in a FFS payment scheme there is no incentive to account for disease management and control, proactive engagement (e.g., telephone, text messaging or home visits) with patient to check treatment progress and/or food insecurities, or establishment of an appropriate team-based care. In addition, risk stratification methodology and associated care do not often match between health plan providers and healthcare delivery organizations. Health plan providers stratify by pure costs as incentivized to save costs (e.g., emergency room care, hospitalizations, high-cost medications) which require different interventions by healthcare delivery organizations to deploy whereas, if done at all, healthcare delivery organizations stratify based on available resources and interventions that are available and needed to improve outcomes.

The initial target risk population will be to focus on the most vulnerable population living with uncontrolled chronic condition(s) who is receiving Medicaid managed care health plans and classified as the top 20% to 30% of need and costs. This will immediately help the disparities seen in healthcare outcomes. The step disclosed herein identifies the chronic condition patient and stratifies 1) each of the one or more individuals based on the ability to engage in the delivery of care program; and 2) each of the one or more individuals by social, behavioral, and medical needs to ensure the right person gets the right intervention at the right time (e.g., number of touches, at home, virtually). The target population step includes 1) establishing how best to identify members of the patient-population; 2) implementing procedures to enable and assess methods for recruitment and retention of members of the patient-population; 3) assessing how to be more patient-centered for each member of the patient-population; 4) continuously evaluating experience of each member of the patient-population to make improvements; and 5) refining risk stratification parameters.

A disclosed method for delivering sustainable healthcare to a patient-population suffering from a chronic condition comprises implementing a value-based payment (VBP) scheme for the sustainable delivery of care to a patient. Traditional and dominant fee for service (FFS) payment schemes are volume based so healthcare delivery organizations are not accountable for things like improving health, equity, emergency room care, and/or hospitalizations. In addition, a FFS payment scheme adopts an a la carte model where there is a fee associated for each service provided, limits the number of times a particular service can be used by a patient, and simply does not cover other services which are not authorized. This leads to a payment scheme that does not provide for all the necessary components needed for a best practice chronic care model. This creates a misalignment in incentives for healthcare plans and healthcare delivery organizations and hinders the ability to develop financially sustainable chronic care programs. This is exacerbated by the fact that large organizations and health plan providers face organizational inertia to shift to an alternative payment system which covers many chronic care costs due to resistance to change and a lack of incentives to change the current payment schemes and business infrastructures. As such, innovators desiring to set up novel programs of care delivery find it tough to insert themselves in the complex systems governing fund distributions and reimbursements, especially, e.g., federal and state-run programs like Medicaid managed care health plans.

A VBP scheme disclosed herein provides a mechanism for payment of start-up costs, time, resources, staffing, appropriate care delivery (such as mental health, self-management, team care) in order to achieve sustainable care for a patient. A VBP scheme moves away from a FFS payment scheme, which is not linked to either quality or value, to a payment plan more in-line to improve health outcomes and cost. For example, a per member per month (PMPM) payment scheme provides for a more comprehensive delivery healthcare services than FFS payment as a patient has access to the needed care at any time without the added obstacle of having to pay for that care or that care not being covered. In addition, a VBP scheme provides for start-up costs pertaining to infrastructure, upfront team hires, IT/tech set-up, training, data management set-up, among other costs. A VBP scheme step includes 1) understanding total cost of care; 2) creating an appropriate patient-population-based payment scheme that is acceptable to the stakeholders; 3) aligning payment operations and how best to make the business case for stakeholders.

A disclosed method for delivering sustainable healthcare to a patient-population suffering from a chronic condition may further comprise a data management step that provides a data infrastructure that facilitates collection, analysis, and reporting to enable transparent data sharing of each member of the patient-population linked to outcomes and cost. A data management step disclosed herein provides a value-based data infrastructure that facilitates analysis and reporting to enable transparent data sharing of patient linked outcomes and cost. The data management step 1) establishes best practices to collect, share, link, manage, analyze, and report data for agreed upon outcomes and cost; and 2) identifies best practices to support a value-based data infrastructure.

A disclosed method for delivering sustainable healthcare to a patient-population suffering from a chronic condition may further comprise a technology platform step that implements an interoperable and flexible healthcare framework that enables and monitors delivery of care and healthcare outcome of each member of the patient-population (e.g., workflow integration, dashboards, analytics, high touch care communication and coordination, education, cost plus health data measurement and management system, virtual care). There is a lack of accessible technology platforms to fully enable efficient team based chronic care delivery virtually and in-person as well as well as to link care processes, health outcomes, and cost data for better data informed decisions. Often, tools are developed within an organization that is proprietary, specific to local needs, expensive to develop, and/or not interoperable.

A technology platform step disclosed herein enables continuous real-time actionable well-informed support for decisions, goal setting, care planning, delivery and management of care, care communication/coordination between the advance primary care team, each member of the patient-population, and/or the community. The technology platform step identifies and prioritizes enabling and enhancing care use cases for each member of the patient-population and each member of the advance primary care team to optimal parameters for the delivery of care program.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compounds, pharmaceutical compositions, or methods and uses disclosed herein.

Example 1

Table of Procedures and Timeline

This example provides a table of exemplary procedures and timeline for implementing a method for delivering sustainable healthcare to a patient-population suffering from a chronic condition as disclosed herein.

| Item | Task | Completed (Y/N) | Y1 Q1 | Y1 Q2 | Y1 Q3 | Y1 Q4 | Y2 Q1 | Y2 Q2 | Y2 Q3 | Y2 Q4 |
|------|------|-----------------|-------|-------|-------|-------|-------|-------|-------|-------|
| 1* | All SOW/Contracts completed | x | | | | | | | | |
| 2 | Contract with research center & Obtain IRB approval | x | | | | | | | | |
| 3* | Stakeholder/leadership engagement, establishment of Stakeholder Steering Committee, & alignment on what success would look like | x | | | | | | | | |
| 4 | Community needs & engagement | x | | | | | | | | |
| 5* | Preparation of assessment with all stakeholders (structure-business, space, culture, etc., processes-care, outcomes-health/equity/experience/utilization/costs, EMR, workflows, refine Stanford Coordinate Care change package, data needs, training materials, surveys, checklists, tech tools, rapid cycle improvement processes, recruitment strategy, consent forms for design team/evaluations, video consent forms, IRB consent form) | x | | | | | | | | |
| 6* | Obtain current state data (costs, health outcomes, processes, structure) from Health Plan & FQHC (to include numbers on T1D, T2D on no insulin, only long acting, and both long and short acting) | x | | | | | | | | |
| 7 | Assessments to understand integration needs | | x | x | x | x | x | x | x | x |

-continued

| Item | Task | Completed (Y/N) | Y1 Q1 | Y1 Q2 | Y1 Q3 | Y1 Q4 | Y2 Q1 | Y2 Q2 | Y2 Q3 | Y2 Q4 |
|---|---|---|---|---|---|---|---|---|---|---|
| 8* | Stakeholder on-going communication, support & problem solve (i.e. data sharing, regulatory hurdles, etc.). At a minimum there will be quarterly stakeholder meetings. | | x | x | x | x | x | x | x | x |
| 9* | Obtain baseline & ongoing data of recruited patients (costs, health, processes, structure) from the care, Health Plan & FQHC | | x | x | x | x | x | x | x | x |
| 10* | Hiring (i.e. coach, data analyst, patient representative, project planner/research assistant) | | x | | | | | | | |
| 11 | Team identification, interviews, culture building, training, coaching, modeling, and feedback + new workflow changes + documentation & collaboration communication techniques for high touch care | | x | x | x | x | x | x | x | x |
| 12 | Care protocols (i.e. dose adjustment, medications) to be refined | | x | | x | | | | x | |
| 13* | Recruitment of patients | | | x | x | | | | | |
| 14 | High touch team-based care delivery (see patient journey) | | x | x | x | x | x | x | x | x |
| 15 | Data system - define measurement system, data elements then test & learn how best to link, share, track, analyze, and develop reports over time for agreed upon outcomes and costs | | x | x | x | x | x | x | x | |
| 16* | Site visits (i.e. fidelity assessments, elements of chronic care model) | | | | | x | x | | x | |
| 17 | Study data collection & trend reporting (qualitative & quantitative) | | x | x | x | x | x | x | x | x |
| 18 | Capture Stakeholder stories (part of qualitative work) | | x | | x | | x | | x | |
| 19 | Rapid cycle improvement processes/Continuous learning/refinement (retention, goals, resources, target population, theory of change, care model, workflow, space, technology, etc.) | | x | x | x | x | x | x | x | |
| 20 | QI data collection & trend reporting | | x | x | x | x | | | | |
| 21* | Develop a cost/savings model/analysis model & funds flow (from agreed upon data to understand payment and total cost of care -Item #5,6,9). | | | x | x | x | x | x | x Refine | x Refine |
| 22* | APM Development: | | | | | | | | | |
| a | Understand current cost of care, scope of service, stratification parameters, Align on top 2-3 APM type to pursue, cost/savings sharing brainstorming | | x | x | | | | | | |
| b | Assess Performance on Utilization/Costs & Care, Refine Scope of Services, Time period covered, trigger for payment | | | | x | x | | | | |
| c | Assess Performance on Utilization/Costs & Care cost/savings sharing alignment, Near end: Align on rate & APM type to trial in full pilot Line item 23 supports this section | | | | | | x | x | | |
| d | Assess Performance on Utilization/Costs & Care, Understand how to operationalize APM | | | | | | | | x | x |
| 23 | Development of high touch team value-based tech platform (to increase team efficiency in communication & care, data collection/analysis, etc.) | | x | x | x | x | | | | |
| 24 | Continuous refinement of change package for full pilot = Implementation workbook | | x | x | x | x | | | | |

-continued

| Item | Task | Completed (Y/N) | Y1 Q1 | Y1 Q2 | Y1 Q3 | Y1 Q4 | Y2 Q1 | Y2 Q2 | Y2 Q3 | Y2 Q4 |
|---|---|---|---|---|---|---|---|---|---|---|
| 25 | Feasibility analysis & writing & evaluation (care + APM) | | | | x | x | | | | |
| 26* | Stakeholder decision to move forward to Full Pilot & understand reasons (Summative Evaluation/Full implementation) | | | | x | x | | | | |
| 27* | Develop full pilot protocol, evaluation, & budget | | | | | x | | | | |

Example 2

Quality Improvement Program

This example describes findings of an on-going quality improvement program employing a method for delivering sustainable healthcare to a patient-population suffering from a chronic condition disclosed herein.

Currently, 54 Medicaid managed insurance care patients have been enrolled into the program. All patients were between the age of 18 and 65 and presented with poorly controlled chronic diabetes as defined by blood levels of HbA1c of greater than 9%. Blood levels of HbA1c and emergency room and hospital utilizations were followed for each patient throughout the course of the program. At the end of five months there was sufficient data on 33 patients to assess the benefit of the sustainable healthcare delivery method disclosed herein.

Figure 4:
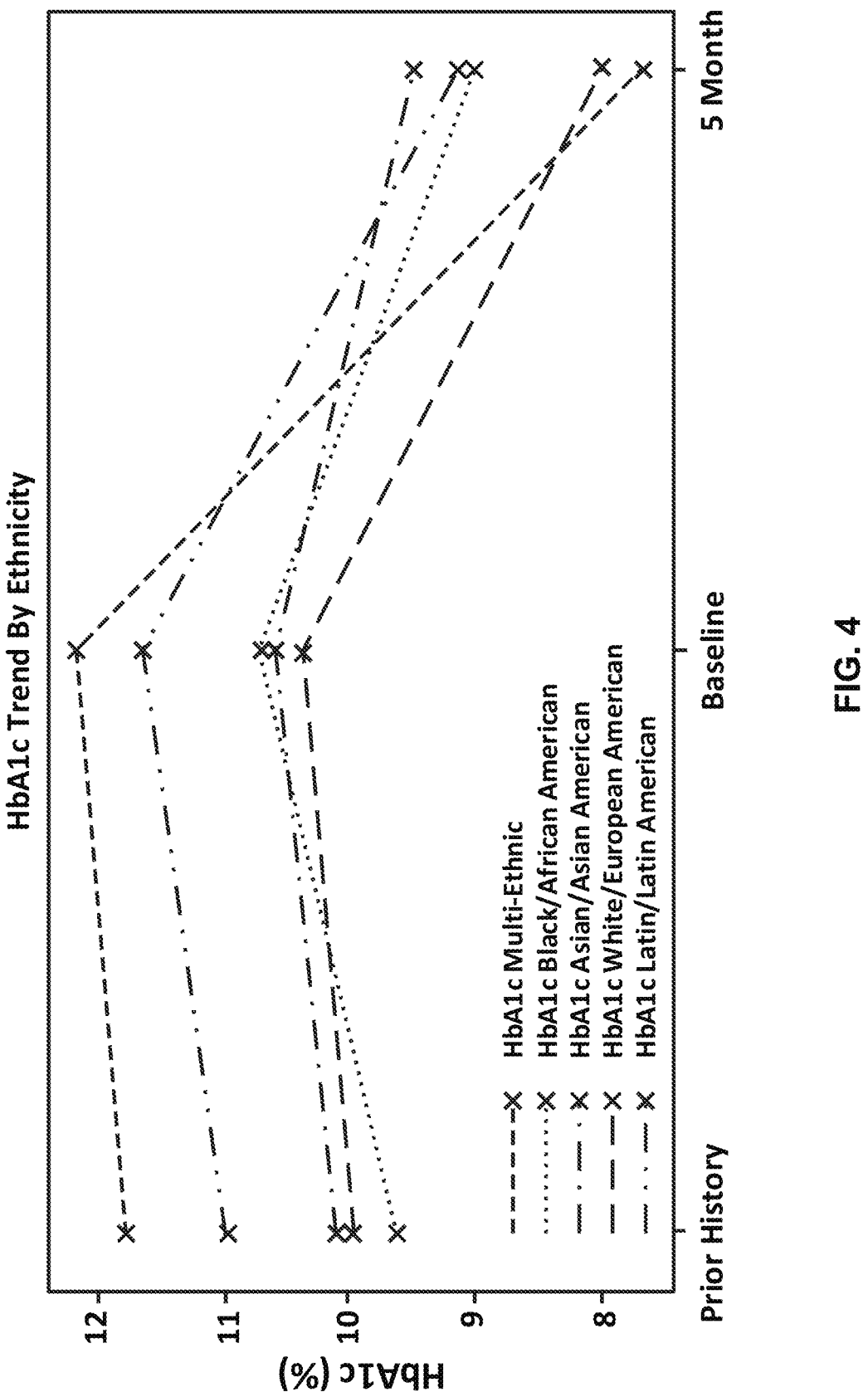
FIG. 4 shows a graph of averaged values of blood levels of A1c stratified by ethnicity.

Investigators detected a significant reduction in HbA1c levels amongst all patients participating in the disclosed sustainable healthcare delivery method as compared to current standard of care methods (Table 1; FIG. 4). For example, Table 1 and FIG. 4 show data from the program stratified by ethnicity. For each ethnic group the disclosed method for delivering sustainable healthcare to a patient-population dramatically improved delivered healthcare. With respect to multi-ethnic patients, patients managed using standard of care methods exhibited on average a HbA1c level of 11.9%. However, the same patients managed under the disclosed healthcare delivery method achieved HbA1c levels of 7.6%. Likewise, with respect to Latin/Hispanic American patients, patients managed using standard of care methods exhibited on average a HbA1c level of 10.9%, while the same patients managed under the disclosed healthcare delivery method achieved HbA1c levels of 9.1%. Decreases of at least 1% in HbA1c levels were also seen in the Black/African American, Asian/Asian American, and White/European American patients.

TABLE 1

| A1c Levels By Ethnicity | | | |
|---|---|---|---|
| | HbA1c Blood Levels | | |
| Ethnicity | Prior History | Baseline | 5 Month |
| Multi-Ethnic | 11.9% | 12.1% | 7.6% |
| Black/African American | 9.6% | 10.8% | 9.0% |
| Asian/Asian American | 10.1% | 10.7% | 9.5% |
| White/European American | 10.0% | 10.4% | 8.0% |
| Latin/Hispanic American | 10.9% | 11.7% | 9.1% |

The level of HbA1c circulating in the blood of a patient is used as a surrogate marker for diabetes control. Studies have shown that for every 1% decrease in HbA1c there is 15% to 45% reduction in complications and about a 20% decrease in deaths. A decrease in 0.5% HbA1c is considered clinically significant. Thus, the fact that patients in this program exhibited between a 1.2% to 4.5% decrease in HbA1c levels is a clinically significant outcome and that the disclosed method is improving the ability of patients to control their diabetes.

In closing, foregoing descriptions of embodiments of the present invention have been presented for the purposes of illustration and description. It is to be understood that, although aspects of the present invention are highlighted by referring to specific embodiments, one skilled in the art will readily appreciate that these described embodiments are only illustrative of the principles comprising the present invention. As such, the specific embodiments are not intended to be exhaustive or to limit the invention to the precise forms disclosed. Therefore, it should be understood that embodiments of the disclosed subject matter are in no way limited to a particular element, compound, composition, component, article, apparatus, methodology, use, protocol, step, and/or limitation described herein, unless expressly stated as such.

In addition, groupings of alternative embodiments, elements, steps and/or limitations of the present invention are not to be construed as limitations. Each such grouping may be referred to and claimed individually or in any combination with other groupings disclosed herein. It is anticipated that one or more alternative embodiments, elements, steps and/or limitations of a grouping may be included in, or deleted from, the grouping for reasons of convenience and/or patentability. When any such inclusion or deletion occurs, the specification is deemed to contain the grouping as modified, thus fulfilling the written description of all Markush groups used in the appended claims.

Furthermore, those of ordinary skill in the art will recognize that certain changes, modifications, permutations, alterations, additions, subtractions, and sub-combinations thereof can be made in accordance with the teachings herein without departing from the spirit of the present invention. Furthermore, it is intended that the following appended claims and claims hereafter introduced are interpreted to include all such changes, modifications, permutations, alterations, additions, subtractions and sub-combinations as are within their true spirit and scope. Accordingly, the scope of the present invention is not to be limited to that precisely as shown and described by this specification.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

The words, language, and terminology used in this specification is for the purpose of describing particular embodiments, elements, steps and/or limitations only and is not intended to limit the scope of the present invention, which is defined solely by the claims. In addition, such words, language, and terminology are to be understood not only in the sense of their commonly defined meanings, but to include by special definition in this specification structure, material or acts beyond the scope of the commonly defined meanings. Thus, if an element, step or limitation can be understood in the context of this specification as including more than one meaning, then its use in a claim must be understood as being generic to all possible meanings supported by the specification and by the word itself.

The definitions and meanings of the elements, steps or limitations recited in a claim set forth below are, therefore, defined in this specification to include not only the combination of elements, steps or limitations which are literally set forth, but all equivalent structure, material or acts for performing substantially the same function in substantially the same way to obtain substantially the same result. In this sense it is therefore contemplated that an equivalent substitution of two or more elements, steps or limitations may be made for any one of the elements, steps or limitations in a claim set forth below or that a single element, step or limitation may be substituted for two or more elements, steps or limitations in such a claim. Although elements, steps or limitations may be described above as acting in certain combinations and even initially claimed as such, it is to be expressly understood that one or more elements, steps or limitations from a claimed combination can in some cases be excised from the combination and that the claimed combination may be directed to a sub-combination or variation of a sub-combination. As such, notwithstanding the fact that the elements, steps and/or limitations of a claim are set forth below in a certain combination, it must be expressly understood that the invention includes other combinations of fewer, more or different elements, steps and/or limitations, which are disclosed in above even when not initially claimed in such combinations. Furthermore, insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. Accordingly, the claims are thus to be understood to include what is specifically illustrated and described above, what is conceptually equivalent, what can be obviously substituted and also what essentially incorporates the essential idea of the invention.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as, e.g., "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising", variations thereof such as, e.g., "comprise" and "comprises", and equivalent open-ended transitional phrases thereof like "including," "containing" and "having", encompass all the expressly recited elements, limitations, steps, integers, and/or features alone or in combination with unrecited subject matter; the named elements, limitations, steps, integers, and/or features are essential, but other unnamed elements, limitations, steps, integers, and/or features may be added and still form a construct within the scope of the claim. Specific embodiments disclosed herein may be further limited in the claims using the closed-ended transitional phrases "consisting of" or "consisting essentially of" (or variations thereof such as, e.g., "consist of", "consists of", "consist essentially of", and "consists essentially of") in lieu of or as an amendment for "comprising." When used in the claims, whether as filed or added per amendment, the closed-ended transitional phrase "consisting of" excludes any element, limitation, step, integer, or feature not expressly recited in the claims. The closed-ended transitional phrase "consisting essentially of" limits the scope of a claim to the expressly recited elements, limitations, steps, integers, and/or features and any other elements, limitations, steps, integers, and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps, integers, and/or features specifically recited in the claim, whereas the meaning of the closed-ended transitional phrase "consisting essentially of" is being defined as only including those elements, limitations, steps, integers, and/or features specifically recited in the claim and those elements, limitations, steps, integers, and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such, the embodiments described herein or so claimed with the phrase "comprising" expressly and unambiguously provide description, enablement, and support for the phrases "consisting essentially of" and "consisting of."

Lastly, all patents, patent publications, and other references cited and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard is or should be construed as an admission that the inventors are not entitled to antedate such disclosure by virtue of prior invention or for any other reason. All statements as to the date or representation as to the contents of these documents are based on the information available to the applicant and do not constitute any admission as to the correctness of the dates or contents of these documents.

The invention claimed is:

1. A method for delivering sustainable healthcare to a patient-population suffering from a chronic condition, the method comprising:

aligning stakeholders for a collaboration involved in delivering care to a patient-population so that the stakeholders collaborate along metrics of care success;

assembling a primary care team for both the patient-population and a community where the patient-population resides to create a delivery of care program for the chronic condition;

identifying the patient-population by assessing one or more individuals suffering from the chronic condition by risk stratification parameters; and defining a value-based payment scheme for the stakeholders to enable the primary care team to treat the chronic condition in the patient-population, wherein the delivery of care program is executed by the primary care team to treat the patient-population and provide healthcare outcomes that address the chronic condition by delivering a personalized treatment to at least one patient in the patient-population to treat the chronic condition, wherein the personalized treatment includes a determination of the chronic condition in the least one patient by the primary care team, and further includes either recommending a medication or a dosage adjustment of an existing medication that reduces blood levels of HbA1C in the at least one patient to treat the chronic condition, and monitoring the blood levels of HbA1C in the at least one patient over time in response to the medication or dosage adjustment, and wherein the value-based payment scheme is implemented to provide compensation to the primary care team for the delivery of the care program, the primary care team receiving payment for the delivery of care program from the at least one patient in the patient population from the value-based payment scheme as the personalized treatment is delivered.

2. The method of claim 1, wherein the stakeholders comprise a healthcare plan provider, a healthcare delivery organization, a state healthcare policy maker, a non-profit healthcare funder, or any combination thereof.

3. The method of claim 2, wherein the healthcare plan provider includes a Medicaid managed care health plan.

4. The method of claim 2, wherein the healthcare delivery organization includes a hospital, a community clinic, a healthcare provider, or any combination.

5. The method of claim 1, wherein the metrics of care success comprise quality of healthcare delivered, schedule of costs and payments, schedule of savings, and distribution of funds.

6. The method of claim 1, wherein alignment of stakeholders comprises 1) aligning goals, measures, and payment to allow scaling and spreading; 2) identifying short term outcome trends in disease specific health outcomes; 3) assessing acceptability of all stakeholders; 4) assessing potential implementation risks and uncertainties to identify mitigations; 5) assessing readiness and ability of stakeholders to change with different processes and systems; 6) assessing community priorities to integrate better.

7. The method of claim 1, wherein the primary care team comprises a local coach, an educator, a behavioral therapist, and a primary care provider.

8. The method of claim 1, wherein the delivery of care program is a proactive delivery of care that is trauma-informed, culturally sensitive, and whole-person.

9. The method of claim 1, wherein the primary care team 1) establishes composition and responsibilities of each member of the primary care team; 2) assesses ideal scope of care to design a best practice care program; 3) develops methods to adapt the best practice care program to the community; 4)

continuously monitors delivery of care to patient-population to identify barriers and best methods to improve delivery of care to each member of the patient-population; 5) continuously monitors a delivery of care to the patient-population to identify barriers and best methods to improve synchronous and asynchronous communication and collaboration between the primary care team, the patient-population, and the community; and 6) assesses program training, workflow integration, protocols, and processes with the community clinic.

10. The method of claim 9, wherein best practice care program comprises 1) prioritizing self-identified goals of each member of the patient-population, 2) establishing patient-led action plans, 3) coordinating and delivering targeted risk reduction and cost-effective care, and 4) creating convenient and improved access for each member of the patient-population by providing in-person and/or virtual care.

11. The method of claim 1, wherein the risk stratification parameters comprise 1) stratifying each of the one or more individuals based on the ability to engage in the delivery of care program; 2) higher costs and 3) stratifying each of the one or more individuals by social, behavioral, and medical needs.

12. The method of claim 1, wherein identification of the patient-population comprises 1) establishing how best to identify members of the patient-population; 2) implementing procedures to enable and assess methods for recruitment and retention of members of the patient-population; 3) assessing how to be more patient-centered for each member of the patient-population; 4) continuously evaluating experience of each member of the patient-population to make improvements; and 5) refining the risk stratification parameters.

13. The method of claim 1, wherein the value-based payment scheme provides a mechanism for payment of start-up costs, resources, staffing, and a delivery of care.

14. The method of claim 13, wherein the start-up costs comprise costs for infrastructure, costs for upfront team hires, costs for IT/tech set-up, costs for training, costs for data management set-up, or any combination thereof.

15. The method of claim 13, wherein the delivery of care comprises one or more of mental health care, self-managed care, and primary care team care to treat the chronic condition.

16. The method of claim 1, wherein the value-based payment scheme comprises 1) understanding total cost of care; 2) creating an appropriate patient-population-based payment scheme that is acceptable to the stakeholders; 3) aligning payment operations and how best to make the business case in current state and new value-based payment for stakeholders; and 4) an assessment of strategies to scale.

17. The method of claim 1, further comprising a data management step that provides a data infrastructure that facilitates analysis and reporting to enable transparent data sharing of each member of the patient-population linked to outcomes and cost.

18. The method of claim 17, wherein the data management step comprises 1) establishing best practices to collect, share, link, manage, analyze, and report data for agreed upon outcomes and cost; and 2) identifying best practices to support a value-based data infrastructure.

19. The method of claim 1, further comprising implementing an interoperable and flexible healthcare framework that monitors delivery of care and healthcare outcome of each member of the patient-population.

20. The method of claim 19, wherein the implementing the interoperable and flexible healthcare framework further comprises providing continuous real-time actionable well-informed support for decisions, goal setting, care planning, delivery and management of care, care communication/coordination between team and/or patient and/or community.

21. The method of claim 19, wherein the implementing the interoperable and flexible healthcare framework further comprises identifying enhanced care use cases for each member of the patient-population and identifying optimal parameters for the delivery of care program for each member of the primary care team.

* * * * *